(12) United States Patent
Alexandre et al.

(10) Patent No.: US 8,070,714 B2
(45) Date of Patent: Dec. 6, 2011

(54) NEEDLELESS SYRINGE PROVIDED WITH MODULAR RESERVOIR

(75) Inventors: Patrick Alexandre, Gray (FR); Bernard Brouquieres, Toulon (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 636 days.

(21) Appl. No.: 12/073,122

(22) Filed: Feb. 29, 2008

(65) Prior Publication Data

US 2008/0154189 A1    Jun. 26, 2008

Related U.S. Application Data

(63) Continuation of application No. 10/296,992, filed as application No. PCT/FR01/01922 on Jun. 20, 2001, now abandoned.

(30) Foreign Application Priority Data

Jun. 22, 2000  (FR) ...................................... 00 07984

(51) Int. Cl.
*A61M 37/00* (2006.01)
*A61M 5/30* (2006.01)

(52) U.S. Cl. .......................................... 604/69; 604/143

(58) Field of Classification Search .............. 604/68–72, 604/82, 87–92, 93.01, 181, 187, 140, 141, 604/143, 145

See application file for complete search history.

(56) References Cited

U.S. PATENT DOCUMENTS

| 2,764,977 | A |   | 10/1956 | Ferguson |
| 4,059,107 | A |   | 11/1977 | Iriguchi et al. |
| 4,124,024 | A | * | 11/1978 | Schwebel et al. ............... 604/69 |
| 4,913,699 | A |   | 4/1990 | Parsons |
| 4,941,880 | A | * | 7/1990 | Burns ........................... 604/143 |
| 5,851,198 | A | * | 12/1998 | Castellano et al. ............. 604/68 |
| 6,406,455 | B1 | * | 6/2002 | Willis et al. ..................... 604/68 |
| 6,758,829 | B2 |   | 7/2004 | Alexandre et al. |
| 7,056,300 | B2 |   | 6/2006 | Alexandre et al. |
| 2002/0099329 | A1 |   | 7/2002 | Castellano |

FOREIGN PATENT DOCUMENTS

| WO | WO 95/03844 | 2/1995 |
| WO | WO 00/10630 | 3/2000 |
| WO | WO 00/48654 | 8/2000 |

* cited by examiner

*Primary Examiner* — Matthew F Desanto
(74) *Attorney, Agent, or Firm* — Oliff & Berridge, PLC

(57) ABSTRACT

The technical field of the invention is that of needleless prefilled disposable syringes, operating with a gas generator, and used for intradermal, subcutaneous and intramuscular injections, of a liquid active principle for therapeutic use in human and veterinary medicine. The inventive needleless syringes use a reservoir (5) consisting of a tube (6) closed by an upstream plug-piston (7) and a downstream plug-piston (8) between which is contained the liquid active principle. Said needleless syringes are characterized in that they are capable of injecting a variable amount of liquid active principle (9) by adapting, through displacement of the downstream plug-piston (8) in the tube (6) the volume included between the two plug-pistons (7,8) to the amount of active principle (9) to be injected.

16 Claims, 2 Drawing Sheets

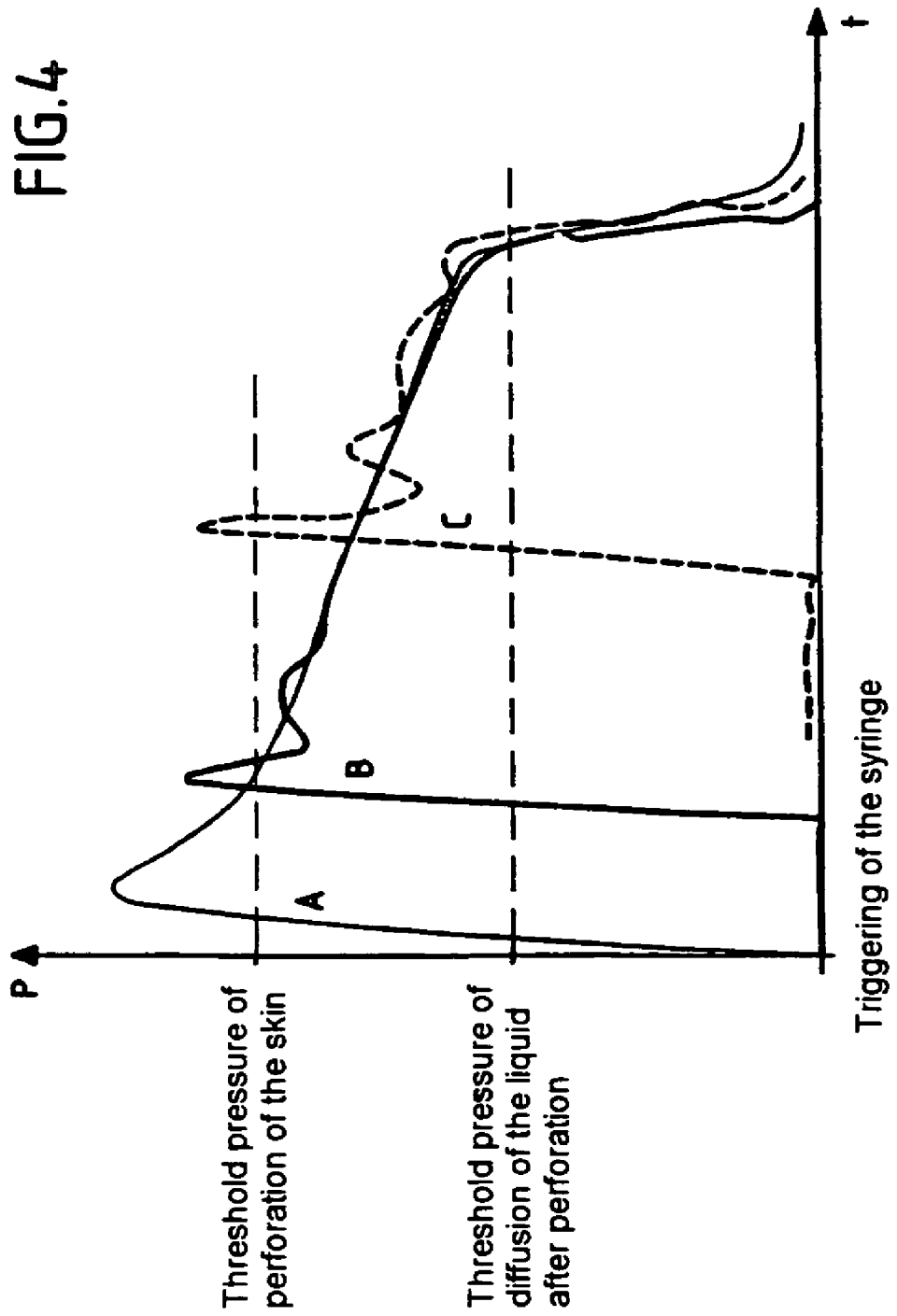

NEEDLELESS SYRINGE PROVIDED WITH MODULAR RESERVOIR

This is a Continuation of application Ser. No. 10/296,992 filed Dec. 2, 2002, which in turn is a National Stage of PCT/FR01/01922 filed Jun. 20, 2001. The disclosure of the prior applications is hereby incorporated by reference herein in its entirety.

The technical field of the invention is that of prefilled and disposable needleless syringes functioning with a gas generator and used for intradermal, subcutaneous and intramuscular injections of liquid active principle for therapeutic use in human or veterinary medicine.

For the injection devices according to the invention, a liquid active principle consists of a more or less viscous liquid, or a mixture of liquid, or a gel. The active principle can be a solid dissolved in a suitable solvent for injection. It can also be represented by a powdered solid in more or less concentrated suspension in a suitable liquid. The particle size of the principle must be compatible with the diameter of the conduits in order to avoid blockages.

The needleless syringes according to the invention have the particular feature of being able to inject a variable amount of liquid active principle by simple modification of their reservoir, all of their other characteristics being integrally retained.

In this way, it is possible to create, both easily and at lower cost, off-the-shelf needleless syringes which are provided with their correct dose of liquid active principle without having to modify their geometry or adapt the gas generator to the dose of liquid active principle to be injected.

Needleless syringes designed to inject variable amounts of liquid active principle already exist and have been the subject of a number of patents.

Mention may be made of the U.S. Pat. No. 4,913,699, for example, which describes a needleless injector intended to contain a variable amount of liquid active principle. The pressure of the liquid leaving the injector is regulated by the difference in cross section between the thrust plunger situated upstream and a plunger stopper of smaller cross section which is accommodated in the terminal injection channel. The patent WO 00/10630 also relates to a needleless injector having, inter alia, the particular feature of expelling a variable amount of liquid active principle by reducing the travel of the thrust plunger. Specifically, the reservoir of active principle, of standard size, is systematically filled to the maximum of its capacity, and the plunger, whose travel can be reduced by a system of pressure-release vents, will ensure injection of only part of the active principle enclosed in the reservoir. After the injection, some liquid active principle remains in the bottom of the reservoir in cases where the travel of the plunger has been reduced.

Finally, mention may be made of the patent 95/03844 which relates to a needleless injector which also has the characteristic of being able to inject a variable amount of active principle by reducing the travel of the thrust plunger. In this case, the screwing of a button causes the displacement of the plunger at the same time as the compression of a spring. When the plunger is at the required position, triggering of the injector thus frees said plunger, which is propelled by the released spring.

The needleless syringes according to the invention permit injection of a variable amount of liquid active principle by simple readjustment of the available volume in the reservoir. This is because, whatever the amount to be injected, the reservoir takes up a constant space within the syringe and it is only its internal volume which is modified, without having to redefine the characteristics of the gas generator or of the thrust plunger in each case, and without having to redimension the different compartments of the syringe. The needleless syringes according to the invention thus contain the exact amount of active principle to be injected and fully retain their efficacy, without anything having to be modified, and without any active principle being left at the bottom of the reservoir after injection.

The subject of the present invention is a needleless syringe comprising a gas generator, a reservoir formed by a tube which is closed off by an upstream plunger stopper and a downstream stopper between which the liquid active principle is contained, and an injection device, characterized in that said syringe is able to inject a variable amount of active principle by means of the fact that, through displacement of a downstream plunger stopper in the tube, the volume included between the two plunger stoppers is adapted to the amount of active principle to be injected.

This is because the needleless syringes according to the invention are dimensioned in such a way as to maintain their injection capacity despite a dimensional modification of their reservoir. Throughout the remainder of the patent, the assembly formed by the two plunger stoppers and the active liquid principle will be called the "column of liquid".

Advantageously, the downstream plunger stopper is at first located entirely within the tube, without protruding from it.

In general, the needleless syringes according to the invention are intended to inject liquid active principle clearly through the skin without loss of said principle on the skin as a result of insufficient speed. The gas generator is thus able, in a first phase, to impart a very high speed to the liquid active principle so as to guarantee the latter an immediate power of penetration through the skin and, in a second phase, to maintain, as a result of almost constant pressure, a sufficient speed of the liquid, so as to guarantee that the latter passes through the skin throughout the duration of injection once perforation has been obtained. The release of the gases by the generator will create a pressurized space between said generator and the upstream plunger stopper due to the displacement of said plunger stopper. This pressurized space, the volume of which increases up to the end of the injection, corresponds to a gas expansion chamber. Said expansion chamber preferably does not exist when the syringe is not functioning. However, it is possible to conceive a needleless syringe according to the invention with a free space already existing between the gas generator and the thrust plunger stopper. Typically, the variation in pressure over time delivered by the gas generator in the space situated between said generator and the upstream plunger stopper causes, in a first stage, the appearance of an instantaneous and very intense pressure peak, then, in a second stage, the establishment of an almost constant pressure which is always greater than the threshold pressure of injection. The term "gas generator" is a generic term designating, without particular distinction, a source of energy which, when it is activated by the user, is able to produce gases in the syringe.

The gas generator is preferably a pyrotechnic gas generator comprising a pyrotechnic charge and an initiation system.

The initiation system advantageously involves a percussion device and a primer. It is also possible to use an initiation system based on a piezoelectric crystal or a roughened area formed by two friction surfaces whose displacement creates an inflammation zone. Compared to a reserve of pressurized gas, a pyrotechnic charge has the advantage of taking up little space and avoids the syringe being permanently subjected to a high internal pressure, including in the storage phase. The pyrotechnic charge is preferably formed by the mixture of a first powder and a second powder, the first powder having a dynamic vivacity greater than that of the second powder. The first powder advantageously has a dynamic vivacity of greater than 8 (MPa·s)$^{-1}$, and the second powder advantageously has a dynamic vivacity of less than 16 (MPa·s)$^{-1}$.

One way of obtaining the pressure profile permitting clean injection of the liquid active principle is in fact to use a pyrotechnic charge consisting of the mixture of a fast-burning powder and a slow-burning powder. A powder is described as "fast-burning" if it has a high dynamic vivacity, and as "slow-burning" if it has a low dynamic vivacity. Thus, the fast-burning powder makes it possible to instantaneously create a very intense pressure peak, while the slow-burning powder, for the rest of the injection, ensures a pressure level which is substantially constant and sufficiently high to allow the liquid active principle to pass through the skin once perforation has been obtained. This type of powder mixture is entirely suitable for the needleless syringes according to the invention. The dynamic vivacity values given above are determined by the formula:

$$L(z) = \frac{1}{P} \cdot \frac{1}{P\max} \frac{(dP)}{dt}$$

where P is the instantaneous pressure corresponding to the state of advance z.
Pmax is the maximum pressure reached.
dP/dt is the derivative of the pressure over time $$z = \frac{P}{P\max}.$$

They correspond to half-combustion values, that is to say for z=0.5 in a manometric chamber under the following conditions:
  chamber volume: 27.8 cm$^3$,
  charging density: 0.036 g/cm$^3$
  powder mass: 1 g.

The powder referred to as slow-burning will always have a dynamic vivacity less than that of the fast-burning powder. The two powders are advantageously mixed loose, that is to say that the two powders are in the state of particles which are mixed randomly, with no particular order, the resulting powder matching the shape of the container in which it is situated, while at the same time forming interstices between the particles. However, it can also be envisaged that at least one of the two powders is present in an ordered or specific manner, for example in the form of a bundle of strands, or in the form of a single particle of considerable size, or even in agglomerated form.

The volume of the reservoir between the two plunger stoppers can preferably vary from 0.1 ml to 2 ml depending on the injection requirements.

The upstream plunger stopper is advantageously situated, in a fixed manner, at one of the two ends of the tube. At least one plunger is preferably lodged between the gas generator and the upstream plunger stopper. The upstream plunger stopper is preferably in contact with the plunger.

The tube is advantageously made of glass and has a thickness of between 0.5 mm and 4 mm and preferably between 1.5 mm and 2.5 mm. The glass tube must be sufficiently thick to withstand a very high internal pressure, without suffering irreversible damage such as fissuring or even bursting open.

The two plunger stoppers are advantageously made of a deformable material. They are in particular obtained by molding of elastomers which are compatible with the liquid active principle over a long duration. These elastomers can for example be chlorobutyl or bromobutyl. The injection device preferably comprises at least two peripheral injection conduits which are situated outside a hollow component serving as receptacle for the downstream plunger stopper, the depth of said component permitting clearance of the inlets of the peripheral conduits when said plunger stopper comes into contact with the bottom of said hollow part.

In terms of its function, the column of liquid moves until the downstream plunger stopper occupies the hollow component. Once blocked in said component, the plunger stopper deforms slightly so as to clear the inlet of the lateral injection conduits and allow the active principle to be expelled. The length of the tube is preferably constant. Specifically, the needleless syringes according to the invention are intended to receive a reservoir of standard size dictated by the length of the tube, the variations of its internal volume situated between the two plunger stoppers being without consequence on its external dimensions. The plunger is advantageously lodged in a hollow body with the same internal diameter as that of the tube and situated in its continuation, said hollow body and said tube being held in an envelope.

The envelope is preferably made of plastic and exerts a slight pressure on the tube so as to increase its resistance to shearing. In this way, the tube is able to withstand greater internal pressures. According to one alternative embodiment of the invention, the reservoir comprising the tube and the two plunger stoppers constitutes a component which is autonomous of said syringe. In other words, the reservoir can be introduced into the syringe or withdrawn at any moment. Likewise, it can be filled separately, with the exact dose of active principle, then introduced into the syringe.

A free space advantageously exists between the downstream plunger stopper and the bottom of the hollow component. Thus, irrespective of the amount of active principle to be injected, and therefore irrespective of the position of the downstream plunger stopper in the tube, the column of liquid will have to undergo a substantial displacement before the injection proper commences. The smaller the amount of product to be injected, the closer is the position of the downstream plunger stopper to that of the upstream plunger stopper, and the longer is the travel of the column of liquid before injection. The presence of a free space between the downstream plunger stopper and the bottom of the receptacle is particularly suitable for the needleless syringes according to the invention. Assuming that the development of the pressure over the course of time in the expansion chamber is adapted to a clean injection of liquid active principle without any losses, it is imperative, for the small doses of active principle to be injected, that the free space between the downstream plunger stopper and the bottom of the receptacle is sufficiently large to allow the column of liquid to be sufficiently accelerated before the start of the injection. This acceleration is made necessary to compensate for the decrease in pressure in the expansion chamber due to the considerable increase of its volume, induced by the displacement of the column of liquid. In other words, for the small amounts of active principle to be injected, the gases emitted by the gas generator will allow the column of liquid to move with an increasing speed throughout its travel. Hence, the greater the displacement of the column, the greater the energy of its impact on the bottom of the receptacle because of the increasing speed, this despite the significant drop in pressure in the expansion chamber.

By way of example, the rise in pressure in the liquid for a reservoir of 0.5 ml occurs at an earlier stage than for a reservoir of 0.2 ml. This is explained by the fact that, for a quantity of 0.5 ml, the displacement travel is smaller than for a quantity of 0.2 ml. The equal intensities of the maximum pressure peaks for the two configurations corresponding to 0.2 ml and to 0.5 ml is justified by the fact that the kinetic energy of impact of the column of liquid compensates for a decrease in the intrinsic thrust of the liquid, on account of a drop in the gas pressure due to an increase of the volume of the space created downstream of the pyrotechnic charge.

The needleless syringes according to the invention make it possible to inject amounts of liquid active principle by simple adaptation of their reservoir, without having to modify their geometry or their size, or even the gas generator, and without having to add other components. They do not therefore require any redimensioning and no supplementary machining, which are sources of increased costs.

In addition, they remain the same size since the reservoir, irrespective of the amount of liquid active principle to be injected, retains its external dimensions.

Finally, adapting the reservoir remains a simple and precise operation, making it possible to have needleless syringes on hand carrying the exact amount of liquid active principle to be injected.

A detailed description of a preferred embodiment of the invention is given below with reference to FIGS. 1 through 4.

FIG. 4 is a simplified diagram comparing the variations in pressure over the course of time, first in the free space created downstream of the pyrotechnic charge, then in the liquid for a reservoir holding 0.5 ml of active principle, and finally in the liquid for a reservoir holding 0.2 ml of active principle.

Figure 1:
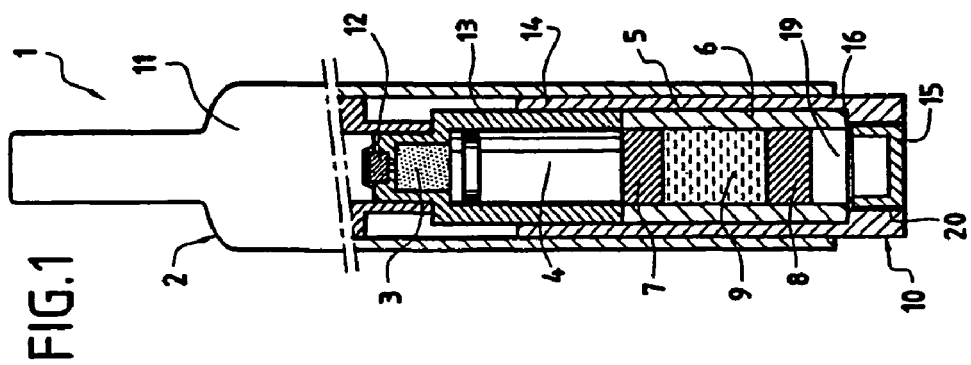
FIG. 1 is a view, in partial longitudinal cross section, of a needleless syringe which has not yet been used.

Referring to FIG. 1, a needleless syringe 1 according to the invention comprises a pyrotechnic gas generator 2 consisting of an initiation system and a pyrotechnic charge 3, a thrust plunger 4, a reservoir 5 formed by a glass tube 6 closed off by an upstream plunger stopper 7 and a downstream plunger stopper 8 between which the liquid active principle 9 is contained, and an injection device 10.

The initiation system involves a percussion device (not shown in FIG. 1) and a primer 12. The percussion device 11 which is triggered by a push button comprises a spring and a weight provided with a striker pin. The weight is blocked by at least one ball wedged between said weight and the push button, and said push button has a circular internal groove.

The pyrotechnic charge 3 is composed of a mixture of a fast-burning powder, for examples a porous powder based on nitrocellulose, and a slow-burning powder, such as a nitrocellulose-based powder with heptatubular particles. The pyrotechnic charge 3 opens into a substantially cylindrical hollow body 13 which is itself continued by the tube 6 of the reservoir 5, said tube 6 having the same internal diameter as that of the hollow body 13. The tube 6 is in continuity with the hollow body 13 and in contact with it, these two components 6 and 13 also having the same external diameter. These are therefore perfectly aligned with one another and are maintained in this configuration by an envelope 14 of plastic material exerting a slight compression on the hollow body 13 and on the tube 6 after assembly. The envelope 14 starts approximately half way along the hollow body 13 and continues beyond the glass tube 6 with a hollow cylindrical front part which forms an additional internal channel adding to the internal channel of the tube 6, said additional channel having a cross section greater than that of the internal channel of the tube 6 and approximately equal to that defined by the imaginary circle representing the half thickness of said tube 6.

The additional channel is able to receive a hollow component 15 consisting of a hollow cylindrical body closed off at one of its two ends by a plane circular surface, said component 15 being similar to a hollow cylindrical stopper. On its outer lateral surface, said hollow body has a series of six longitudinal grooves which are parallel to one another and uniformly spaced.

The component 15 is engaged in the additional channel so that:
 the plane circular surface of said component 15 is flush with the free end of the front part of the envelope 14,
 the outer lateral wall of the hollow cylindrical body of said component 15 is in contact with the inner lateral wall of the additional channel so that the longitudinal grooves form peripheral injection conduits 20,
 a passage 16 remains between the free end of the tube 6 and the free end of the hollow cylindrical body of said component 15.

The hollow cylindrical body 13 into which the pyrotechnic charge 3 opens is entirely occupied by the thrust plunger 4. The upstream plunger stopper 7 is flush with one of the two ends of the glass tube 6 and said thrust plunger 4 is in contact both with the pyrotechnic charge 3 and with said upstream plunger stopper 7.

The downstream plunger stopper 8 is situated set back from the other end of the tube 6 and the liquid active principle 9 is enclosed in the space of said tube 6 delimited by the two plunger stoppers 7, 8. The two plunger stoppers 7, 8 are made of elastomer-based deformable material. The thrust plunger 4 is made of nondeformable material. Downstream of the downstream plunger stopper 8 there is a free space 19 formed by the internal channel of that part of the tube 6 situated downstream of the downstream plunger stopper 8 and by the internal volume of the component 15 similar to a hollow plug, said free space 19 being in communication with the outside of the syringe 1 by way of the six peripheral injection conduits 20.

The injection device 10 comprises the front part of the envelope 14 and the hollow component 15 engaged in said front part, and it thus includes the free space 19 situated downstream of the downstream plunger stopper 8 and the six peripheral injection conduits 20.

The method of functioning of this preferred embodiment of the invention is as follows.

The user positions the syringe 1 in such a way that its end bears against the skin of the patient to be treated. A pressure applied to the push button causes it to slide along the syringe 1 until the groove comes level with the ball which blocks the weight. The ball, disengaging in the groove, releases the weight which, under the action of the spring which releases, is propelled toward the primer 12, with the striker pin leading.

The primer 12 which is thus initiated causes the firing of the pyrotechnic charge 3.

Under the effect of the combustion of the fast-burning powder, the thrust plunger 4 is abruptly displaced in the internal channel of the hollow body 13 and of the tube 6, provoking the displacement of the column of liquid. A gas expansion chamber 17 is thus created between the pyrotechnic charge 3 and the thrust plunger 4.

Figure 2:
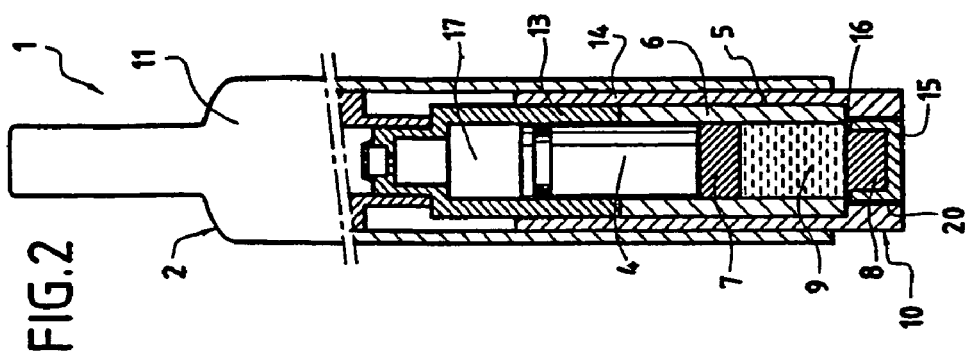
FIG. 2 is a view, in partial longitudinal cross section, of the syringe from FIG. 1 during use, the injection not yet having started.

FIG. 2 shows the syringe 1 during use, more precisely at the instant when the column of liquid abuts against the bottom of the receptacle formed by the internal volume of the hollow component 15 similar to a hollow plug. Comparison of FIGS.

Figure 3:
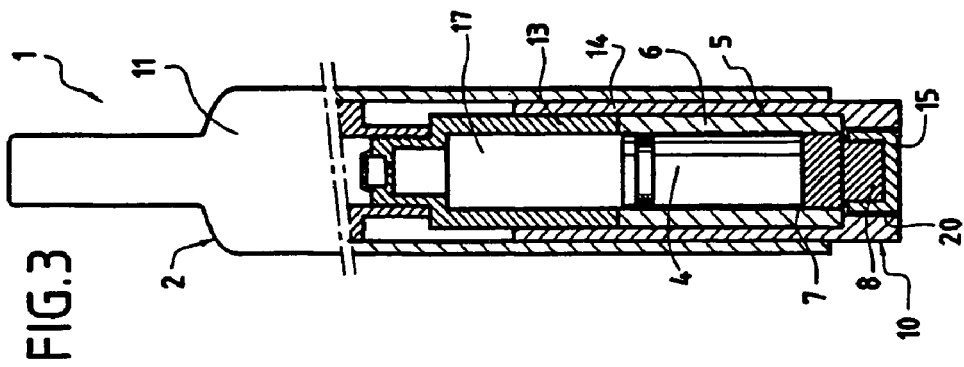
FIG. 3 is a view, in partial longitudinal cross section, of the syringe from FIG. 1 at the end of use, the injection being completed.

1 and 2 shows the distance traveled by said column with an increasing speed prior to its impact. The downstream plunger stopper 8 which occupies the whole of the receptacle is crushed slightly, thereby freeing the passage 16 serving as an inlet to the channels 20 of the injection device 10, while the upstream plunger stopper 7 moves closer to the trapped downstream plunger stopper 8. The liquid active principle 9 is thus expelled with a pressure which is substantially decreasing, but still greater than the threshold pressure of diffusion of the liquid after perforation of the skin, until the two plunger stoppers 7, 8 come into contact with one another, as is shown in FIG. 3.

During the displacement of the upstream plunger stopper 7, the volume of the expansion chamber 17 has continually increased. At the end of injection, there is no liquid active principle left in the reservoir 5 of the syringe 1.

By way of example, referring to curve A in the diagram in FIG. 4, the pressure variation, over the course of time, induced by the combustion of the pyrotechnic charge 3 in the space created between said charge 3 and the plunger 4 causes the instantaneous appearance of a very intense peak, which is followed by a phase of progressive and continued reduction. The appearance of the very intense peak takes place after about 1 ms, and the phase of reduction for its part lasts for about twenty milliseconds. Curve B, which illustrates the pressure variation over the course of time of the liquid active principle 9 at the outlet of a reservoir 5 initially containing 0.5 ml, also causes the appearance of a very intense peak, followed by a phase of reduction. The peak is created a certain time after the syringe is triggered, this delay corresponding to the travel of the column of liquid before the downstream plunger stopper 8 arrives in abutment at the bottom of the hollow component 15.

This peak, which remains very intense, is the result of the conjunction of two phenomena:
   the intrinsic thrust of the liquid 9 by the gas pressure,
   the impact of the column of liquid on the bottom of the hollow component 15. Since said column moves with increasing speed in the reservoir 5, the impact occurs in an acceleration phase, thereby affording a surplus energy which promotes the expulsion of the liquid.

The phase of pressure reduction which follows is substantially aligned with that observed in the free space created between the pyrotechnic charge 3 and the plunger 4.

Finally, curve C which represents the pressure variation over the course of time of the liquid active principle 9 at the outlet of a reservoir 5 initially containing 0.2 ml shows a very intense pressure peak followed by a phase of continued reduction. The peak arrives later than that for curve B since the travel of the column of liquid is greater. The peaks of curves B and C have approximately the same intensity because the intrinsic thrust of the liquid 9 by the gas pressure—which is lower in the case of the reservoir containing 0.2 ml because of a drop in gas pressure due to a more considerable increase in the volume of the space situated between the pyrotechnic charge 3 and the plunger 4—is compensated by an increase in the kinetic energy of impact induced by a greater displacement of the column of liquid at increasing speed.

The comparative diagram in FIG. 4 shows that, by simple displacement of the downstream plunger stopper 8, the needleless syringe 1 according to the invention conserves its full efficacy, first in terms of perforation of the skin, then in terms of diffusion of the liquid 9.

What is claimed is:

1. A method of preparing a needleless syringe for use, the needleless syringe including a gas generator, a reservoir consisting of a tube closed by an upstream plunger stopper and a downstream plunger stopper between which a liquid active principle is to be contained, the reservoir being able to have a variable volume by moving the downstream plunger stopper in the tube, and an injection device, the method comprising:
   providing a variable volume of liquid active principle in the needleless syringe between the upstream plunger stopper and the downstream plunger stopper;
   arranging the downstream plunger stopper when the needleless syringe is ready for injection so that a free space is left between the downstream plunger stopper and the injection device that allows for acceleration of the liquid active principle prior to ejection from the injection device by the gas generator;
   forming a pyrotechnic charge by mixing a first powder and a second powder, the first powder having a dynamic vivacity greater than that of the second powder; and
   calculating a length of the free space so that the liquid active principle reaches the desired injection speed when entering the injection device, wherein the length of free space is variable.

2. The method as claimed in claim 1, further comprising: situating the upstream plunger stopper, when ready for injection, at the top of the tube close to the gas generator.

3. The method as claimed in claim 2, further comprising: lodging at least one plunger between the gas generator and the upstream plunger stopper.

4. The method as claimed in claim 3, further comprising: contacting the upstream plunger stopper with the at least one plunger.

5. The method as claimed in claim 2, wherein the reservoir comprising the tube, the upstream plunger stopper and the downstream plunger stopper constitutes a component which is autonomous of the needleless syringe.

6. The method as claimed in claim 1, wherein the tube is made of glass and has a thickness of between 0.5 mm and 4 mm.

7. The method as claimed in claim 6, wherein a length of the tube is constant.

8. The method as claimed in claim 1, further comprising: calculating a length of the free space along a longitudinal axis of the needleless syringe so that the liquid active principle reaches a desired injection speed when entering the injection device.

9. The method as claimed in claim 1, wherein the gas generator is a pyrotechnic gas generator comprising a pyrotechnic charge and an initiation system.

10. The method as claimed in claim 1, further comprising: selecting the first powder to have a dynamic vivacity of greater than 8 $(MPa \cdot s)^{-1}$, and selecting the second powder to have a dynamic vivacity of less than 16 $(MPa \cdot s)^{-1}$.

11. The method as claimed in claim 1, wherein the provided variable volume of the reservoir between the two plunger stoppers is from 0.1 ml to 2 ml.

12. The method as claimed in claim 1, wherein the upstream plunger stopper and the downstream plunger stopper are made of a deformable material.

13. The method as claimed in claim 1, wherein the injection device comprises at least two peripheral injection conduits which are situated outside a hollow component serving as a receptacle for the downstream plunger stopper, a depth of the hollow component permitting clearance of inlets of the at least two peripheral conduits when the downstream plunger stopper comes into contact with a bottom of the hollow component.

14. The method as claimed in claim 1, wherein a length of the tube is constant.

15. The method as claimed in claim 1, further comprising:

increasing a free space length with a decrease in liquid active principle volume so that travel of the liquid active principle is made to increase before ejection from the injection device.

16. A method for injecting an active principle, comprising:

preparing a needleless syringe for injection use according to the method as claimed in claim 1;

activating the gas generator; and accelerating the liquid active principle through the free space left between the downstream plunger stopper and the injection device to inject the active principle via the injection device.

* * * * *